(12) United States Patent
Gahr et al.

(10) Patent No.: US 9,207,204 B2
(45) Date of Patent: Dec. 8, 2015

(54) METHOD AND APPARATUS FOR DETERMINING INFORMATION CONCERNING PRESENCE OF CONSTITUENTS OF A LIQUID SAMPLE WITH OXYGEN DEMAND

(75) Inventors: Achim Gahr, Goldbach (DE); Rudolf Bauer, Dieburg (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 443 days.

(21) Appl. No.: 12/801,130

(22) Filed: May 25, 2010

(65) Prior Publication Data

US 2010/0294672 A1    Nov. 25, 2010

Related U.S. Application Data

(60) Provisional application No. 61/213,285, filed on May 26, 2009.

(30) Foreign Application Priority Data

May 25, 2009 (DE) .......................... 10 2009 026 453

(51) Int. Cl.
*G01F 1/64* (2006.01)
*G01N 27/327* (2006.01)
*G01N 27/42* (2006.01)
*G01N 27/30* (2006.01)
*G01N 33/18* (2006.01)

(52) U.S. Cl.
CPC .............. *G01N 27/42* (2013.01); *G01N 27/308* (2013.01); *G01N 33/1806* (2013.01)

(58) Field of Classification Search
CPC ................................ G01N 27/327; G01F 1/64
USPC ..................................................... 204/403.15
See application file for complete search history.

(56) References Cited

U.S. PATENT DOCUMENTS 5,324,666 A * 6/1994 Siepmann et al. .............. 436/62
5,399,247 A 3/1995 Carey et al.
(Continued)

FOREIGN PATENT DOCUMENTS

| DE | 44 24 355 C2 | 1/1996 |
|---|---|---|
| DE | 694 10 576 T2 | 2/1999 |
| EP | 0282441 | 9/1988 |

(Continued)

OTHER PUBLICATIONS

Bard and Faulkner Electrochemical Methods 1980 John Wiley and Songs pp. 341-345.*

(Continued)

*Primary Examiner* — Luan Van
*Assistant Examiner* — Steven Rosenwald
(74) *Attorney, Agent, or Firm* — Bacon & Thomas, PLLC

(57) ABSTRACT

In a method and apparatus for determining information concerning the presence of ingredients with oxygen demand in a liquid sample, especially for determining the chemical oxygen demand of a liquid sample, especially a water, or wastewater, sample, by means of electrochemical oxidation of ingredients of the liquid sample, oxidation of ingredients of the liquid sample occurs on a boron doped, diamond electrode.

11 Claims, 1 Drawing Sheet

(56) References Cited

U.S. PATENT DOCUMENTS 6,106,692 A * 8/2000 Kunimatsu et al. .......... 205/775
2005/0226774 A1 10/2005 Kounaves

FOREIGN PATENT DOCUMENTS

| EP | 0 428 514 B1 | | 5/1991 | |
|----|----|----|----|----|
| EP | 0 834 739 A2 | | 4/1998 | |
| GB | 1314917 | * | 7/1970 | ............. G01N 27/44 |
| WO | WO 2006/061192 A1 | | 6/2006 | |

OTHER PUBLICATIONS

Weiss et al. Journal of Applied Electrochemistry, vol. 38 (No. 3), 329-337.*
Brillas et al. (Chemosphere 58, 2005, 399-406).*
English translation of DE 1996137704.*
Johnson et al. (Anal. Chem. 40, 1968, p. 482).*
English Translation of International Preliminary Report on Patentability.
Environmental Sensing Potential With Boron-Doped Diamond Microdisc and Macro-Electrodes, Ph. Rychen, A. Perret, et al. Jan. 1, 2001, XP008035711.
Hattori S. et al., Electrolytic Decomposition of Amaranth Dyestuff Using Diamond Electrodes, Journal of Applied Electrochemistry, Jan. 1, 2003.
Yu et al., Amperometric Determination of Chemical Oxygen Demand Using Boron-Doped Diamond (BDD) Sensor, Electrochemistry Communication, Sep. 1, 2007.

* cited by examiner

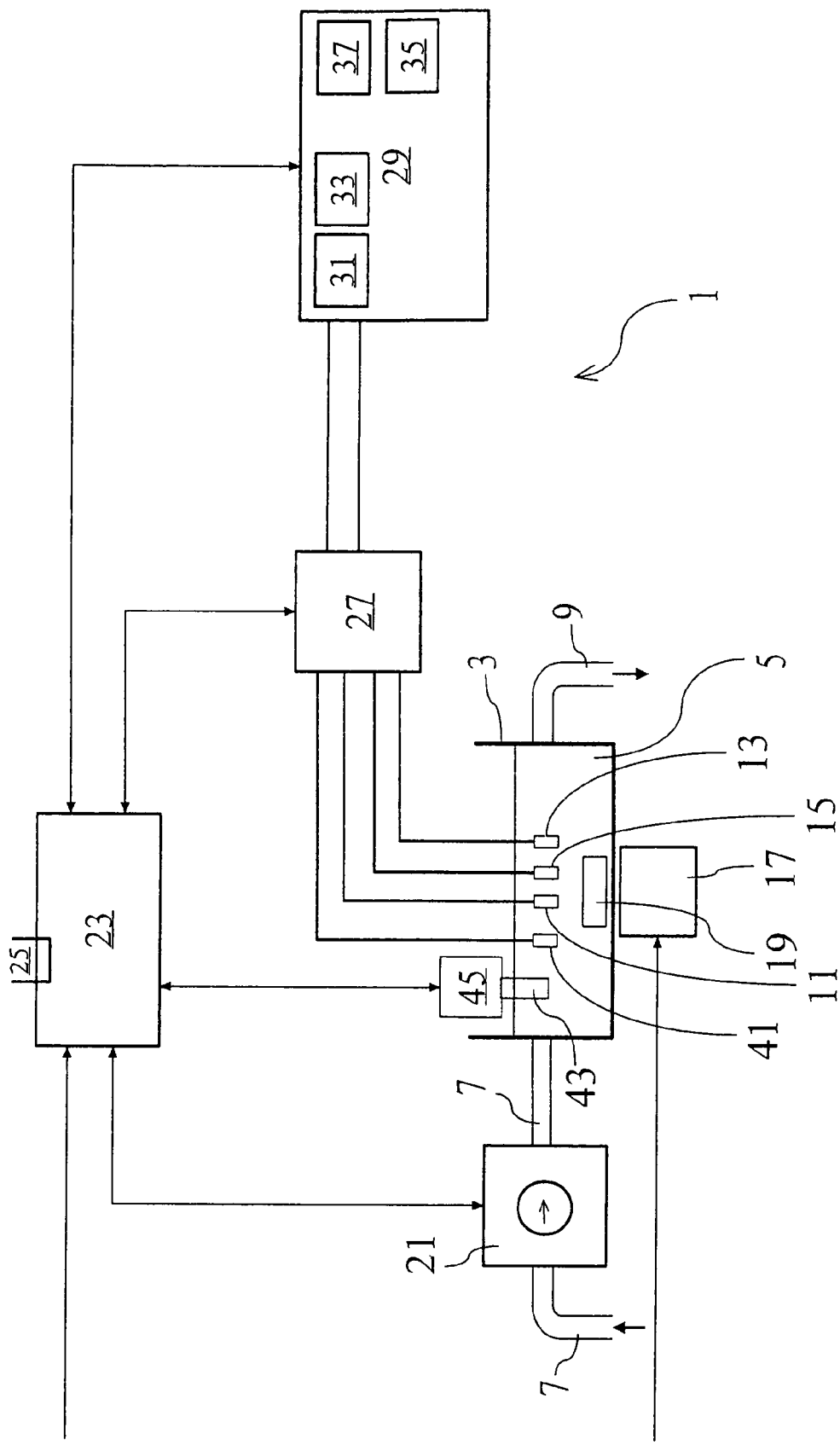

METHOD AND APPARATUS FOR DETERMINING INFORMATION CONCERNING PRESENCE OF CONSTITUENTS OF A LIQUID SAMPLE WITH OXYGEN DEMAND

CROSS-REFERENCE TO RELATED APPLICATION

This application is a Nonprovisional which claims the benefit of U.S. Provisional Application No. 61/213,285, which was filed on May 26, 2009.

TECHNICAL FIELD

The invention relates to a method and an apparatus for determining information concerning the presence of constituents of a liquid sample with oxygen demand, especially for determining the chemical oxygen demand of a liquid sample, especially a water, or wastewater, sample.

BACKGROUND DISCUSSION

The determining of chemical oxygen demand (COD) plays an important role in the investigation especially of aqueous samples and the evaluation of waste water quality. This is true, for example, in the control of waste water treatment in a clarification plant or in the monitoring of waste waters both in the case of introduction of such into other waters, as well as also at the inlet or outlet of clarification plants.

In the case of known wet chemical methods for determining the COD value, oxidation of the organic materials dissolved in a liquid sample occurs by chemical reaction with an added oxidizing agent, e.g. $K_2MnO_4$ or $K_2Cr_2O_7$. For masking disturbing ions, e.g. chloride, frequently, a mercury salt is added.

These methods have, in the meantime, been set down in DIN-standards (German Institute for Standardization). Disadvantageous in the case of these methods is that they do not work continuously, since the sample to be examined must, as a rule, be reacted at least one hour long with the oxidizing agent under increased temperature, before the consumption of the oxidizing agent and therefrom COD value of the sample can be ascertained. Furthermore, the used chemicals, especially $K_2Cr_2O_7$, are poisonous and potentially strongly environmentally damaging, so that, on the one hand, complex precautionary measures must be undertaken, in order that the chemicals not get into the environment, while, on the other hand, a great effort for the disposal of the consumed samples and chemicals must be made.

There are, therefore, a number of approaches for determining chemical oxygen demand without the addition to the sample to be examined of reagents acting as oxidizing agent.

In German Patent, DE 2 135 949 A1, a measuring method is described, in the case of which water electrolysis is applied, wherein the hydrogen developing electrode is separated by a membrane from the sample to be examined, into which the oxygen developing electrode is immersed, wherein via the membrane a charge carrier exchange can occur. The measuring principle rests on the concept that the oxygen amount theoretically produced by the electrical current flow is compared with the actually produced oxygen. In such case, the theoretically produced oxygen amount is ascertained via the used quantity of charge, while the actually produced oxygen amount is measured as a pressure increase. If the actually formed oxygen amount falls behind the theoretically expected value, then the reason for this is either that charge was consumed for direct oxidation of substances contained in water, or the developed oxygen was partially consumed as oxidizing agent. This method requires a relatively complex measurement setup. Furthermore, a continuous measuring is not directly possible with this method.

European Patent, EP 282 441 B1 describes a further electrochemical method for determining COD by unspecific electrochemical oxidation of ingredients dissolved in a water sample at controlled potential, wherein, via a lead dioxide, working electrode, electrical current flowing through the aqueous solution is measured and provides a measure for the quantity of material converted at the electrodes per unit time. The method rests on the concept that on a lead dioxide anode preferably a forming of OH-radicals (OH.) and ozone (O3) occurs, which are two very reactive oxidizing agents, and that their rate of formation and therewith also their consumption caused by oxidation of the ingredients of the sample solution can be registered by measuring the electrical current flow through the lead dioxide electrode.

German Patent, DE 196 37 704 A1 describes a similar method, which is supposed to enable the provision of extensive information concerning the nature of the ingredients present in the sample responsible for the COD. In such case, a three electrode circuit with a lead dioxide electrode as working electrode is used. Basic idea of the method described there is to vary the potential on the lead dioxide electrode while measuring the associated electrical current level arising between the lead dioxide electrode and the counterelectrode and flowing through the sample, or alternatively to vary the electrical current level of the electrical current flowing through the sample and measure the associated potential on the lead dioxide electrode and so to obtain a number of measured values. By evaluation of the measured value curves, for example, by comparison with reference measured value curves for certain typical sample compositions, qualitative information on the presence of slightly or difficultly oxidizable materials in the sample can be made.

A disadvantage of lead dioxide electrodes is that they must be regularly regenerated, since a passivating cover layer can form on them during operation. Furthermore, there is the danger that, due to chemical or mechanical action on the lead dioxide electrode, poisonous lead compounds can get into the sample, e.g. a wastewater or drinking water sample, and possibly escape into the environment.

SUMMARY OF THE INVENTION

An object of the invention is thus to provide a method for the initially named field of the invention, which overcomes the disadvantages of the state of the art, and to provide an apparatus, which is suitable for performing the method. Especially, the method and corresponding apparatus should not require regeneration of the working electrode, or at least the frequency of regeneration steps should be reduced, wherein simultaneously also endangering of the environment should be reduced.

This object is achieved by a method for establishing information concerning the presence of ingredients with an oxygen demand in a liquid sample, especially for determining the chemical oxygen demand of a liquid sample, especially a water, or wastewater, sample, by means of electrochemical oxidation of the ingredients of the liquid sample, wherein oxidation of the ingredients of the liquid sample occurs on a boron doped, diamond electrode.

Boron doped, diamond electrodes are known per se. They are used, for example, for removal of undesired components from gases or liquids, e.g. from water, per oxidation. Such a method for the oxidative elimination of undesired components from a gas stream is described, for example, in German Patent, DE 103 165 759.

According to the invention, boron doped, diamond electrodes are used to provide, by oxidation of constituents of a liquid sample, information concerning the presence in the liquid sample of ingredients with an oxygen demand, especially to determine the COD value of the liquid sample. Boron doped, diamond electrodes are chemically highly inert. That means, on the one hand, that the forming of passivating cover layers on the electrode during operation is strongly reduced, so that, in comparison to a lead dioxide electrode, a regeneration of the diamond electrode need not be so frequently performed, or, depending on which type of samples is examined, also regeneration measures can be completely eliminated. On the other hand, in the case of the application of a boron doped, diamond electrode, the endangering of the environment by poisonous chemicals, e.g. by dissolving of electrode material, is excluded. The method can especially also be used for determining the TOC value (TOC =total organic carbon), when the method is conducted in such a manner, that all organic compounds contained in the sample are oxidized.

In an embodiment, the boron doped, diamond electrode comprises an electrically conductive, base material, e.g. a metal or half metal, especially niobium, silicon, silicon carbide, graphite, tungsten or tantalum, which has a coating of boron doped diamond, especially of a thickness between 1 to 50 μm, especially 1 to 20 μm, for example, 5 μm.

The concentration of boron in the coating can be 1000 to 10000 ppm, preferably 2000 to 5000 ppm.

The boron doped, diamond electrode can be operated as working electrode of a two, or three, electrode circuit. A two electrode circuit has, besides the working electrode, which is here formed by the boron doped, diamond electrode, a counterelectrode. A three electrode circuit has three electrodes, namely, besides the working electrode, which here, again, is formed by the boron doped, diamond electrode, a counterelectrode and a reference electrode. In such case, the three electrode circuit is so operated, that the reference electrode is not or, at least only minimally, flowed through by electrical current. The terms "two electrode circuit" and "three electrode circuit" are used here to designate a connection of the boron doped, diamond electrode as a working electrode relative to a counterelectrode, on the one hand, or a connection of the boron doped, diamond electrode as a working electrode relative to an electrical current bearing counterelectrode and an essentially non-electrical current bearing, reference electrode for performing electrochemical, e.g. potentiostatic or galvanostatic, measuring methods for determining material conversion, on the other hand. The apparatus for performing the here described method can, however, supplementally to these two, or three electrodes, comprise other electrodes, e.g. another metal electrode for determining the redox potential of the liquid, or a pH-electrode, as will be explained further below.

The oxidation can occur at a controlled potential of the boron doped, diamond electrode. For example, the controlled potential can be selected in such a manner, that OH-radicals (OH.) and/or ozone ($O_3$) are formed on the electrode in the liquid sample, especially the water sample. Both species are, as is known, highly reactive oxidizing agents and, consequently, able to oxidize ingredients, e.g. organic components, present in the liquid sample with oxygen demand.

In order to develop information concerning the amount of ingredients, which have an oxygen demand, contained in the liquid sample, especially the COD value of the liquid sample, the quantity of material converted per unit time on the boron doped, diamond electrode can be ascertained from the electrical current flowing via the boron doped, diamond electrode connected as a working electrode of a two, or three, electrode circuit. This provides a measure for the amount of ingredients with an oxygen demand in the liquid sample. From the converted quantity of material, especially the chemical oxygen demand of the liquid sample can be ascertained. When the oxidation is performed in such a manner that all organic ingredients present in the sample are completely oxidized, then also the TOC value can be ascertained.

In a refined embodiment, the boron doped, diamond electrode can be operated sequentially at at least two different, predetermined potentials. At each predetermined potential, an electrical current, measured value of the electrical current flowing at the predetermined potential through the liquid sample is measured. And, the electrical current, measured values are placed in a predetermined relationship to one another, especially their quotient or their difference or a measurement curve is formed, especially a measurement curve of the electrical current, measured values as a function of the predetermined potential.

From such a relationship placing, the presence of ingredients with an oxygen demand in the liquid sample, especially the chemical oxygen demand of the liquid sample, can be derived.

For example, in this manner, in a special method variant, a potential curve, e.g. a linear rise of the potential, can be applied to the boron doped, diamond electrode connected as a working electrode and the associated curve of the electrical current level of the electrical current flowing via the working electrode registered. This method is also referred to as voltammetry with linear potential ramp (technical expression: linear sweep voltammetry). When not just a linear rise, or linear fall of the potential, but instead, a triangular voltage, which rises or falls from a predetermined first potential linearly to a second potential and then falls or rises back linearly to the first potential, is applied, the method is referred to as cyclic voltammetry. Linear sweep voltammetry or cyclic voltammetry in the case of the here described method are preferably applied in a potential range, in which OH-radicals and/or ozone are formed on the boron doped, diamond electrode as working electrode.

In an alternative method variant, a predetermined electrical current level of an electrical current flowing through the sample via the boron doped, diamond electrode serving as a working electrode can be set and controlled. The potential established at the predetermined electrical current level on the boron doped, diamond electrode is measured. From the measured potential, information concerning the presence of ingredients in the liquid sample with an oxygen demand, especially the chemical oxygen demand of the liquid sample, can be derived. This method variant and its refinements described in the following are referred to here and in the following as the "galvanostatic" method. The earlier described method variant, in the case of which the applied potential to the working electrode is controlled and the electrical current level of the electrical current flowing via the working electrode through the liquid sample is measured, is referred to, in contrast thereto, as the "potentiostatic" method.

Also this alternative method variant can be refined, in that, one after the other, i.e. sequentially, at least two different predetermined electrical current magnitude values of an electrical current flowing through the liquid sample via the boron doped, diamond electrode serving as a working electrode can be set. At each predetermined electrical current level, a potential, measured value of the potential established, in each case, on the boron doped, diamond electrode is measured, and the potential, measured values are placed in a predetermined relationship to one another, especially their quotient or their difference or a measurement curve is formed, especially a measurement curve of the potential, measured values as a function of the predetermined electrical current level. From the relationship placing, information concerning the presence of ingredients in the liquid sample with an oxygen demand, especially the chemical oxygen demand of the liquid sample, is derived.

Information, for example, as regards type and concentration or other properties, such as e.g. the oxidizability of ingredients with an oxygen demand contained in the liquid sample, or the COD value of the liquid sample, can be derived from the result of the placing in relationship, from the measurement curve or from one or more electrical current, or potential, measured values, which can be ascertained as previously described. Thus, a value obtained as a result of the placing in relationship, or a measurement curve or an electrical current, or potential, measured value is compared with at least one stored reference value or at least one stored reference curve, and, on the basis of the comparison, a quantitative evaluation of the occurrence of ingredients in the liquid sample with oxygen demand, especially the determining of the chemical oxygen demand of the liquid sample, is performed. The reference values, or reference curves, can be e.g. calibration values, or calibration curves, won from measurements with liquid samples of known composition.

When a measurement curve has been ascertained, e.g. a measurement curve of the electrical current flowing at the working electrode as a function of the applied potential or a measurement curve of the potential measured on the working electrode as a function of the electrical current flowing through the liquid sample, by integration of the measurement curve, especially when such was won by a linear variation of the potential on the working electrode, or the electrical current level flowing via the work electrode, the material conversion on the working electrode and therewith the amount of ingredients with an oxygen demand present in the sample can also be deduced.

In a method variant, products formed on the boron doped, diamond electrode, especially oxidation products, are quantitatively detected.

For example, OH-radicals and/or ozone formed on the boron doped, diamond electrode can be quantitatively detected and/or, with the assistance of additional means, the consumption of OH-radicals and/or ozone can be monitored.

Thus, for example, the concentration of the oxidation products, especially OH. and/or $O_3$, formed on the boron doped, diamond electrode, can be ascertained by determining the redox potential. For this, for example, an additional metal electrode, for example, a platinum pin, can be used. The potential occurring on this additional metal electrode can be measured relative to the potential of the reference electrode of the three electrode circuit or relative to an additional reference electrode.

Furthermore, the consumption of ozone formed on the boron doped, diamond electrode for the oxidation of sample constituents with an oxygen demand can be registered by monitoring the oxygen concentration in the liquid sample by means of an oxygen sensor, since ozone reacts to O2 in the case of the oxidation of sample constituents. The consumption of OH-radicals can be registered by monitoring the pH-value of the sample, e.g. by means of a pH-sensor, e.g. a conventional glass electrode embodied as a single-rod measuring chain. OH-radicals can furthermore also be captured with capture molecules added to the sample, and the therefrom resulting concentration change of the capture molecules monitored by means of an additional sensor; this is referred to in the following in short as "OH.radical sensor".

Additionally, a redox sensor, for example, a single rod sensor with a metal working electrode, e.g. of gold, and a metal counterelectrode, e.g. likewise of gold and a reference electrode in a three electrode circuit can be used for determining the redox potential or for the voltammetric detection of substances, such as e.g. ozone or also of disturbing ions, such as e.g. chloride ions present in the liquid sample. For monitoring the chloride concentration, also a conventional chloride ion sensor can be used. By means of one or more ion selective electrodes, which can be embodied either as a single-rod measuring chain with its own reference electrode or as individual membrane electrodes, wherein the potential forming on the membrane electrode as a function of the concentration of the ions to be detected can be measured relative to the reference electrode of the three electrode circuit, other ions in the sample to be analyzed can be detected. The results obtained by means of the redox sensor or the other optional additional sensors, e.g. the ozone, or chloride, concentration in the liquid sample, can be taken into consideration in determining the information concerning sample constituents with an oxygen demand, especially in the case of determining the COD value.

The above defined object is furthermore achieved by an apparatus for determining the occurrence of ingredients with an oxygen demand in a liquid sample, especially the chemical oxygen demand of the liquid sample, comprising:

at least one boron doped, diamond electrode;

a counterelectrode, or a counterelectrode and a reference electrode;

means for setting a predetermined potential on the boron doped, diamond electrode relative to the reference electrode and/or the counterelectrode, or for setting a predetermined electrical current level of an electrical current flowing through the liquid sample between the counterelectrode and the boron doped, diamond electrode; and means for registering the electrical current level of an electrical current flowing through the liquid sample or a potential occurring on the boron doped, diamond electrode.

In an embodiment, the means for setting a predetermined potential on the boron doped, diamond electrode relative to the reference electrode and/or the counterelectrode, or for setting a predetermined electrical current level of an electrical current flowing through the liquid sample between the counterelectrode and the boron doped, diamond electrode is provided by a potentiostat or a galvanostat. The potentiostat can function as voltage source, which is so embodied, that it drains the electrical current, which must flow through the working electrode, but, however, is not permitted to flow through the reference electrode, via a third electrode, the counterelectrode, into the liquid sample. The electrical current free, reference electrode delivers a defined and stable reference potential. The potentiostat serves, thus, in the case of a potentiostatic measuring, for applying a controlled, defined potential to the working electrode, and also for registering the electrical current level of the electrical current flowing through the liquid sample at the predetermined potential. In the case of a galvanostatic measuring, an electrical current flow through the liquid sample between counterelectrode and working electrode is held constant and the occurring potential value registered. Today, obtainable potentiostats are frequently so embodied, that they also can be applied as a galvanostat. The terminology applied in the following, "potentiostat/galvanostat", refers to an electronic circuit arrangement, which permits a potentiostatic operation, a galvanostatic operation or a selectively potentiostatic or galvanostatic operation of a connected two, or three, electrode circuit.

Furthermore, the apparatus includes, preferably, a control system for automatic setting of a plurality of predetermined potential, or electrical current, magnitude values and registering the associated electrical current level, or potential, measured values.

The apparatus can, furthermore, include an evaluating system for the relationship placing of the electrical current level, or potential, measured values, which has an evaluation program memory for storing at least one result-value of the relationship placing and a data memory for storing the electrical current level, or potential, measurement values, as well as a processing unit. The evaluating system can furthermore include a display unit for displaying the evaluation result and/or an interface for forwarding the result-value to a superordinated unit.

The reference electrode can be an Hg/Hg2+ electrode, e.g. an Hg/HgSO$_4$ electrode, or an Ag/AgCl electrode.

The counterelectrode can be, like the working electrode, a boron doped, diamond electrode, or a metal electrode, especially an electrode of platinum, gold, silver or titanium.

The apparatus can, furthermore, include means for detection of products, especially oxidation products, formed by electron transfer on the boron doped, diamond electrode connected as a working electrode. For example, the means can be suitable to detect OH-radicals and/or ozone, or to monitor their consumption.

The means for detection of oxidation products formed on the boron doped, diamond electrode connected as a working electrode can comprise, for example, a redox electrode. This can be in the form of a metal electrode, wherein the potential occurring on the metal electrode relative to the reference electrode of the apparatus or relative to a supplementally provided, reference electrode is measurable.

For monitoring the ozone consumption, the apparatus can furthermore comprise an additional oxygen sensor. Furthermore, for monitoring OH. consumption, an additional pH-sensor, for example, a glass electrode embodied as a single-rod measuring chain, can be a component of the apparatus. Alternatively, also an OH-radical sensor embodied as above described can be provided. The apparatus can comprise other sensors for determining additional substances, such as chloride or other ions contained in the sample, as previously described.

The apparatus can be embodied as an immersion sensor, wherein the apparatus can be immersed into the liquid sample such that all electrodes of the two, or three, electrode circuit and possibly supplementally present electrodes or sensors, are sufficiently immersed into the liquid sample for forming a measured value. Alternatively, the apparatus can also be embodied in the form a measuring cell or flow measuring cell, into which the liquid sample is conveyed. In the measuring cell, the needed electrodes and other additional sensors can be fixedly installed.

BRIEF DESCRIPTION OF THE DRAWING

The invention will now be explained in greater detail on the basis of the example of an embodiment illustrated in the drawing, the sole figure of which shows as follows:

FIG. 1 is a schematic representation of an apparatus for determining information concerning ingredients with an oxygen demand in a liquid sample.

DETAILED DISCUSSION IN CONJUNCTION WITH THE DRAWING

In the case of the apparatus 1 schematically illustrated in FIG. 1 for determining information concerning the ingredients with an oxygen demand in a liquid sample, there are located in a measuring cell 3, into which the liquid sample 5 to be analyzed can be supplied through an inlet 7 and from which the liquid sample 5 can be drained back out through an outlet 9, three electrodes, namely a working electrode 11, a counterelectrode 13 and a reference electrode 15. The liquid sample 5 contained in the measuring cell 3 can be stirred by means of a magnet stirrer 17, which, by the production of a rotating magnetic field, can cause a rod magnet 19 present in the measuring cell 3 to rotate.

The working electrode 11 includes an electrically conductive carrier, which at least in the surface region, which is immersed in measurement operation into the liquid sample 5, is coated with a boron doped, diamond coating. The counterelectrode 13 can be identically constructed; it can, however, also be formed simply of sheet metal, especially platinum or titanium sheet metal. The reference electrode 15 is a reference electrode of second type with diaphragm, which is embodied, for example, in the form of an Hg/Hg2+ system.

A pump 21 serves for metering the liquid sample, for example, a wastewater sample, from a sample supply (not shown), into the measuring cell 3. The pump 21 can be embodied, for example, in the form of a peristaltic pump. For calibrating the apparatus 1, the pump 21 can convey a liquid sample 5 of known chemical oxygen demand, or known composition, into the measuring cell 3. For cleaning the measuring cell 3, the pump 21 can, furthermore, supply a cleaning liquid via the supply line 7. In given cases, a second supply line (not shown) can be provided, by which diluting water is introduced into the measuring cell 3. This can be of advantage, for example, when the liquid samples to be analyzed have a very high COD. The diluting water can be supplied into the measuring cell 3 by means of the pump 21 or by means of an additional pump (not shown).

For automatic control of the apparatus 1, a control unit 23 is provided, which, in usual manner, has a program memory and a data memory. Controlled by a stored, control program, a liquid sample 5 is continuously or cyclically supplied via the supply line 7 into the measuring cell 3 and, in given cases, diluted with diluting water. The control unit 23 has available an interface 25 for the connection of a computer or of a data carrier for the transmission of data, via which the control program can be updated, or via which parameter data for the control program can be written into the data memory of the control unit 23.

The addition of diluting water for samples with high COD is controlled on the basis of the evaluation result (see further below), wherein the degree of dilution is automatically taken into consideration in the evaluation.

The working electrode 11, the counterelectrode 13 and the reference electrode 15 are connected with the corresponding inputs of a potentiostat/galvanostat 27, which can be operated as a potentiostat or as a galvanostat. In operation as a potentiostat, a controlled predetermined potential is applied between reference electrode 15 and working electrode 11 and the electrical current flow through the working electrode 11 measured. In operation as a galvanostat, in contrast, the electrical current between working electrode 11 and counterelectrode 13 is controlled to a predetermined electrical current level and the potential occurring on the working electrode 11 relative to the reference electrode 15 is measured. Of course, also a potentiostat operable exclusively as a potentiostat, or a galvanostat operable exclusively as a galvanostat, can be applied. Then, however, the possible measurement modes of the apparatus 1 are reduced.

The potentiostat/galvanostat 27 is connected with a microprocessor, evaluating unit 29, which registers the electrical current, or potential, measured values of the potentiostat/galvanostat 27 and forwards such to the control unit 23. The evaluating unit 29 can also include a display unit 31, on which the measured potential, or electrical current, measured values are directly displayed. The evaluating unit 29 can be a separate unit separable from the potentiostat/galvanostat 27. Alternatively, the evaluating unit 29 and the potentiostat/galvanostat 27 can be embodied as a single component.

The evaluating unit 29 includes a measured value memory 33, in which the, in given cases, sequentially registered, electrical current, or potential, measured values are stored under the address of the respective, predetermined potential or electrical current. A processing unit 35 processes the stored measured values by means of an evaluation program stored in an evaluation program memory 37.

The evaluation program compares electrical current level, or potential, measured values with stored values from calibration measurements with liquid samples of known composition. It, furthermore, places, for example, the electrical current level, measured values obtained in potentiostatic measurement operation at different potentials, or the potential, measured values obtained in galvanostatic measurement operation at different electrical current levels, in relationship to one another or ascertains measurement curves of the electrical current level, measured values as a function of the potential applied to the boron doped, diamond electrode or measurement curves of the potential, measured values as a function of the electrical current level of the electrical current flowing through the liquid sample 5 via the boron doped, diamond electrode. From the placing in relationship, or from the measurement curves, the evaluation program generates result-values (which can also comprise the entire measurement curve).

The output signal of the processing unit, which can be output via the display unit 31 or to the control unit 23, comprises result-values output by the evaluation program. The result-values provide information concerning the presence of oxidizable ingredients in the liquid sample. In the control unit 23, the result-values can be compared with reference values or evaluated based on a model. From the result-values, especially, the COD of the liquid sample can be ascertained, for example, by comparison of the result-values with corresponding result-values of calibration solutions with known COD values.

In order to be able to provide refined information concerning the concentrations, or the properties, of ingredients with oxygen demand contained in the liquid sample 5, a redox electrode 41 is provided, which is immersed into the liquid sample 5. The redox electrode 41 can be, for example, of sheet metal or a metal pin, e.g. of platinum, gold or titanium. The potentiostat/galvanostat 27 registers the potential occurring on the redox electrode 41 relative to the reference electrode 15. The redox electrode 41 can be provided with an additional reference electrode as a single rod sensor, in given cases, even in a three electrode circuit with an additional gold-, platinum- or titanium-counterelectrode. A single rod sensor of such type with integrated counterelectrode can also be used for determining ozone or also additional substances present in the sample, such as e.g. disturbing ions, for example, chloride ions. The measured values of the redox electrode 41, or the single rod sensor, are forwarded to the control unit 23 and can be taken into consideration for determining information concerning ingredients of the liquid sample 5 with oxygen demand, or determining COD of the liquid sample 5.

Furthermore, an additional oxygen sensor 43 can be provided, which monitors concentration of oxygen in the liquid sample 5. In this way, decomposition of ozone produced on the boron doped, diamond electrode 11 can be monitored, which, again, provides a measure for the oxidizing conversion in the sample liquid. The oxygen sensor 43 is connected with a transmitter for energy, and data, transmission, which converts the primary signals of the oxygen sensor 43 and outputs to the control unit 23. The control unit 23 controls, conversely, the oxygen sensor 43 via the transmitter 45. Instead of the oxygen sensor 43, or supplementally, a pH-sensor can be provided, for example, a conventional glass electrode embodied as single-rod measuring chain, which is connected in analogous manner, via a transmitter, or directly, with the control unit 23.

The invention claimed is:

1. A method for determining information concerning the presence of ingredients with an oxygen demand in a liquid sample by means of electrochemical oxidation of ingredients of the liquid sample, comprising the steps of:
   providing a boron doped, diamond electrode;
   placing the boron doped, diamond electrode in the sample;
   providing a reference electrode;
   placing the reference electrode in the sample;
   permitting oxidation of the ingredients of the liquid sample on the boron doped, diamond electrode, at a controlled potential of the boron doped diamond electrode;
   ascertaining from electrical current flowing via the boron doped, diamond electrode connected as a working electrode of a three electrode circuit, the quantity of material converted per unit time on the working electrode; and
   ascertaining from the quantity of the material converted per unit time on the working electrode the chemical oxygen demand of the liquid sample, wherein:
   the boron doped, diamond electrode is operated sequentially at least two different, predetermined potentials, and at each predetermined potential a measured value of the electrical current flowing through the liquid sample at the predetermined potential is measured;
   the electrical current measured values are placed in a predetermined relationship to one another;
   the quotient or difference or a measurement curve of the electrical current, measured values is formed, as a function of the predetermined potentials;
   from the relationship placing, a chemical oxygen demand (COD) in the liquid sample is derived;
   oxidation products formed on the boron doped, diamond electrode are quantitatively detected: and
   the concentration of the oxidation products formed on the boron doped, diamond electrode is ascertained by determining redox potential by ascertaining a potential occurring at an additional metal electrode, which is immered into the liquid sample.

2. The method as claimed in claim 1, wherein:
   the boron doped, diamond electrode includes an electrically conductive base material, of niobium, silicon, silicon carbide, graphite, tungsten or tantalum, which has a coating of boron doped diamond, at a thickness between 1 to 50 µm.

3. The method as claimed in claim 2, wherein:
   boron is present in the coating at 1000 to 10000 ppm.

4. The method as claimed in claim 1, wherein:
the boron doped, diamond electrode is operated as a working electrode of a three electrode circuit comprising said working electrode, a counterelectrode and said reference electrode.

5. The method as claimed in claim 1, wherein:
the controlled potential is selected in such a manner that OH-radicals and/or ozone is formed in the liquid sample; and
the liquid sample is a water sample.

6. The method as claimed in claim 1, wherein:
the boron doped, diamond electrode is operated at one of said predetermined potentials and the electrical current level of the electrical current flowing through the liquid sample is measured; and
from the measured electrical current level information concerning the presence of ingredients with a chemical oxygen demand in the liquid sample is derived.

7. The method as claimed in claim 1, wherein:
a potential is moved linearly and a corresponding measurement curve of the electrical current level of the electrical current flowing through the boron doped, diamond electrode is recorded as a function of the linearly moved potential.

8. The method as claimed in claim 1, wherein:
oxidation products are formed on the boron doped, diamond electrode; and
said oxidation products are ozone and/or OH-radicals and said products are quantitatively detected using a pH-sensor, an OH-radical sensor or an oxygen sensor.

9. A method for determining information concerning the presence of ingredients with an oxygen demand in a liquid sample by means of electrochemical oxidation of ingredients of the liquid sample, comprising the steps of:
providing a boron doped, diamond electrode;
placing the boron doped, diamond electrode in the sample; and
permitting oxidation of the ingredients of the liquid sample on the boron doped, diamond electrode,
wherein:
a predetermined electrical current level of an electrical current flowing through the liquid sample via the boron doped diamond electrode connected as a working electrode of a two, or three, electrode circuit is set;
the potential occurring at the predetermined electrical current level on the boron doped, diamond electrode is measured; and
from the measured potential, information concerning the presence of the ingredients of the liquid sample with an oxygen demand is derived, wherein:
sequentially, at least two different predetermined electrical current magnitude values of an electrical current flowing through the liquid sample are set;
at each predetermined electrical current level, a potential measured value of potential occurring on the boron doped, diamond electrode is measured;
the potential measured values are placed in a predetermined relationship to one another by forming the quotient or difference of the measured values or by forming a measurement curve of the measured values as a function of the predetermined electrical current level;
from the relationship placing a chemical oxygen demand (COD) in the liquid sample is derived;
oxidation products formed on the boron doped, diamond electrode are quantitatively detected; and
the concentration of the oxidation products formed on the boron doped, diamond electrode is ascertained by determining redox potential by ascertaining a potential occurring at an additional metal electrode, which is immersed into the liquid sample.

10. The method as claimed in claim 9, wherein:
a value or a measurement curve obtained as a result of the relationship placing is compared with at least one stored reference value or at least one stored form of comparison curve; and
on the basis of this comparison, a quantitative evaluation of the chemical oxygen demand of the liquid sample is performed.

11. The method as claimed in claim 9, wherein:
oxidation products formed on the boron doped, diamond electrode are quantitatively detected, said oxidation products are ozone and/or OH-radicals and the ozone and/or OH-radicals are quantitatively detected using a pH-sensor, an OH-radical sensor or an oxygen sensor.

* * * * *